United States Patent [19]
Vidal et al.

[11] Patent Number: 6,063,136
[45] Date of Patent: May 16, 2000

[54] COMPOSITIONS CONTAINING PYRROLO-OXAZOLE COUPLERS FOR DYEING KERATIN FIBERS AND DYEING METHODS

[75] Inventors: Laurent Vidal, Paris; Gérard Malle, Villiers-sur-Morin, both of France

[73] Assignee: L'Oréal S.A., Paris, France

[21] Appl. No.: 09/242,932

[22] PCT Filed: Aug. 22, 1997

[86] PCT No.: PCT/FR97/01522

§ 371 Date: Feb. 26, 1999

§ 102(e) Date: Feb. 26, 1999

[87] PCT Pub. No.: WO98/08487

PCT Pub. Date: Mar. 5, 1998

[30] Foreign Application Priority Data

Aug. 26, 1996 [FR] France .................................. 96 10447

[51] Int. Cl.⁷ ...................................................... A61K 7/13
[52] U.S. Cl. ........................... 8/409; 8/407; 8/423; 8/572; 8/574
[58] Field of Search .............................. 8/409, 423, 572, 8/574, 407

[56] References Cited

U.S. PATENT DOCUMENTS

| | | | |
|---|---|---|---|
| 4,620,850 | 11/1986 | Bachmann et al. | 8/406 |
| 5,091,517 | 2/1992 | Naef | 534/752 |
| 5,380,340 | 1/1995 | Neunhoeffer et al. | 8/409 |

FOREIGN PATENT DOCUMENTS

| | | |
|---|---|---|
| 0 026 474 | 4/1981 | European Pat. Off. . |
| 0 335 834 | 10/1989 | European Pat. Off. . |
| 0 722 710 | 7/1996 | European Pat. Off. . |
| 0 879 953 | 11/1998 | European Pat. Off. . |
| 2 074 731 | 10/1971 | France . |
| 2 586 913 | 3/1987 | France . |
| 2 359 399 | 6/1975 | Germany . |
| 2 429 195 | 2/1976 | Germany . |
| 3 843 892 | 6/1990 | Germany . |
| 4 133 957 | 4/1993 | Germany . |
| 63-169571 | 7/1988 | Japan . |
| 7-98489 | 4/1995 | Japan . |
| 7-244361 | 9/1995 | Japan . |
| 7-325375 | 12/1995 | Japan . |
| 1 026 978 | 4/1966 | United Kingdom . |
| 1 153 196 | 5/1969 | United Kingdom . |
| WO 94/08969 | 4/1994 | WIPO . |
| WO 94/08970 | 4/1994 | WIPO . |

OTHER PUBLICATIONS

Mohamed I. Ali et al., "Reactions with Thiazolo[3,2–b]–s–trazol–3(2H)–ones", Journal f. prakt. Chemie. Band 318, Heft 1, 1976, pp. 12–18. No month available.

von Freidrich Asinger et al., Über die Umstzung von α–Oxo–thionamiden mit Aldiminen, II²⁾, Liebigs Ann. Che., 744, 1971, pp. 51–64. No month available.

L.L. Bennett, Jr., et al., Synthesis of Potential Anticancer Agents. IV. 4–Nitro–and 4–Amino–5–imidazole Sulfones, Journal of the American Chemical Society, vol. 79, No. 9, May 5, 1957, pp. 2188–2191.

Victor Israel Cohen, "A new Method of Synthesis of Some 2–Aryl and 2–Heterocyclic Benzimidazole, Benzoxazole and Benzothiazole Derivatives", Journal of Heterocyclic Chemistry, vol. 16, No. 1, Jan. 1979, pp. 13–16.

Mohamed Hilmy Elnagdi et al., "Reactions with Cyclic Amidines II. The Behaviour of Cyclic Amidines Toward Ethoxycarbonyl and Aroyl Isothiocyanates", Journal of Heterocyclic Chemistry, vol. 16, No. 1, Jan. 1979, pp. 61–64.

Henryk Foks et al., "Synthesis and Biological Activity of Thiazolo–1,2,4–Triazoles", Acta Poloniae Pharmaceutica—Drug Research, vol. 52, No. 5, 1995, pp. 415–420. No month available.

S.A. Hiller et al., "Electron Density Distribution in Heterocyclic Systems With Two Adjacent Nitrogen Atoms", Chemistry of Heterocyclic Compounds, vol. 3, No. 1, Jan.–Feb. 1967, pp. 93–96.

Eric Hoggarth, "Compounds related to Thiosemicarbazide. Part I. 3–Phenyl–1:2:4–triazole Derivatives", Journal of The Chemical Society, Part II, 1949, pp. 1160–1163. No month available.

Eser Ilhan et al., "Synthese von 6–Benzyliden–2–(α,α–diphenyl–α–hydroxyacetyl)–thiazolo[3,2–b]–s–triazol–5–onen als potentiell biologisch wirksame Stoffe", Arch. Pharm. (Weinheim), 327, 1994, pp. 825–826. No month available.

Jiro Kinugawa et al., "Studies on Fungicides. VI. Synthesis of Thiocyanatopyrazoles", Chemical & Pharmaceutical Bulletin, vol. 12, No. 1, Jan. 1964, pp. 23–33.

Ferenc Korodi et al., "Fused 1,2,4–Triazole Heterocycles. III. Syntheses and Structures of Novel [1,2,4]Triazolo[1,3] Thiazinoquinolines", Heterocyclic Communications, vol. 1, No. 4, 1995, pp. 297–306. No month available.

(List continued on next page.)

*Primary Examiner*—Caroline D. Liott
*Attorney, Agent, or Firm*—Finnegan, Henderson, Farabow, Garrett & Dunner, L.L.P.

[57] ABSTRACT

The present invention relates to a composition and a dyeing process for the dyeing of keratinous fibers, in particular of human hair, having, as coupler, at least one compound of formula:

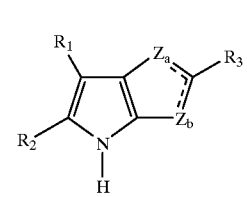

(I)

where $Z_a$ and $Z_b$, which are different from one another, represent an oxygen or nitrogen atom,
and at least one oxidation base.

33 Claims, No Drawings

OTHER PUBLICATIONS

David A. Rosenfeld et al., Methyl 2,6–Anhydro–α–D–altroside and Other New Derivatives of Methyl α–D–Altroside, Journal of the American Chemical Society, vol. LXX, May–Aug. 1948, pp. 2201–2215.

S. Syed Shafi et al., "Studies on Biological Active Heterocycles Part 1. Synthesis and Antibacterial Activity of Some 2,5–Disubstituted–1,3,4–Oxadiazoles, 1,3,4–Thiadiazole, 1,2,4–Triazole, and 4–Thiazoloidinone", Indian Journal of Heterocyclic Chem., vol. 5, Oct.–Dec. 1995, pp. 135–138.

Edwin E. Wiegand et al., Polyphosphoric Acid Cyclization of Acetamidoketone to 2,5–Dimethyl–1,3–oxazoles, International Journal of Methods in Synthetic Organic Chemistry, 1970, pp. 648–649. No month available.

J.F. Willems et al., The Preparation of 5–Substituted 1,2, 4–Triazoline–3–Thiones and of Alkylene and Arylene 5,5'–bis–1,2,4–Triazoline–3–Thiones, Bull. Soc. Chim, Belges, 75, 1955, pp. 358–365. No month available.

Chemical Abstracts, vol. 133, No. 12, Sep. 1995, Abstract of JP 07–98,489.

STN International, Karlsruhe File Caplus, Sep. 1995, Abstact of JP 7–244,361.

English language Derwent Abtract of DE 2 359 399, Jun. 1975.

English language Derwent Abtract of DE 2 429 195, Feb. 1976.

English language Derwent Abtract of DE 3 843 892, Jun. 1990.

English language Derwent Abtract of EP 0 722 710, Jul. 1996.

English language Derwent Abtract of FR 2 074 731, Oct. 1971.

English language Derwent Abtract of FR 2 586 913, Mar. 1987.

English language Derwent Abtract of JP 2019576, Jan. 1990.

English language Derwent Abtract of JP 7–98489, Apr. 1997.

English language Derwent Abtract of JP 7–244361, Sep. 1995.

English language Derwent Abtract of JP 7–325375, Dec. 1995.

COMPOSITIONS CONTAINING PYRROLO-OXAZOLE COUPLERS FOR DYEING KERATIN FIBERS AND DYEING METHODS

The subject-matter of the invention is a composition for the oxidation dyeing of keratinous fibres, in particular human keratinous fibres, such as hair, comprising, as coupler, at least one pyrrolooxazole compound and at least one oxidation base.

It is known to dye keratinous fibres and in particular human hair with dyeing compositions comprising oxidation dye precursors, in particular ortho- or para-phenylenediamines, ortho- or para-aminophenols, or heterocyclic compounds, generally known as oxidation bases. Oxidation dye precursors or oxidation bases are colourless or weakly coloured compounds which, in combination with oxidizing products, can give rise, by an oxidative coupling process, to coloured and colouring compounds.

It is also known that it is possible to vary the shades obtained with these oxidation bases by combining them with couplers or colouring modifiers, the latter being chosen in particular from aromatic meta-diamines, meta-aminophenols, meta-diphenols and certain heterocyclic compounds, such as indole compounds.

The variety of the molecules involved as oxidation bases and couplers makes it possible to obtain a rich palette of colours.

The so-called "permanent" colouring obtained by virtue of these oxidation dyes has, however, to satisfy a certain number of requirements. Thus, it must be without disadvantage toxicologically and it must make it possible to obtain shades with the desired intensity and behave well in the face of external agents (light, bad weather, washing, permanent waving, perspiration or rubbing).

The dyes must also make it possible to cover white hair and, finally, be as non-selective as possible, that is to say make it possible to obtain the smallest possible differences in colouring along the same keratinous fibre, which can in fact be differently sensitized (i.e. damaged) between its tip and its root.

The Applicant Company has now just discovered that it is possible to obtain powerful novel dyes, which are not very selective, which are particularly resistant and which are capable of generating intense colourings in varying shades, by using, as couplers, pyrrolooxazole compounds in the presence of an oxidation base.

This discovery forms the basis of the present invention.

The subject-matter of the invention is a composition for the oxidation dyeing of keratinous fibres and in particular of human keratinous fibres, such as hair, characterized in that it comprises, in a medium appropriate for dyeing:

as coupler, at least one pyrrolooxazole compound of following formula (I) and/or at least one of their addition salts with an acid:

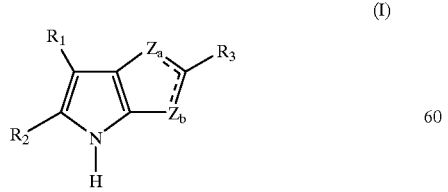

(I)

in which:
$R_1$ represents a hydrogen atom; a halogen atom, such as bromine, chlorine or fluorine; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy or methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy or 1-naphthyloxy); an acyloxy radical (such as, for example: acetoxy, propanoyloxy, benzoyloxy, 2,4-dichlorobenzoyloxy, ethoxyoxaloyloxy, pyruvoyloxy, cinnamoyloxy or myristoyloxy); an arylthio radical (such as, for example: phenylthio, 4-carboxyphenylthio, 2-ethoxy-5-tert-butylphenylthio, 2-carboxyphenyl-thio or 4-methanesulphonylphenylthio); an alkylthio radical (such as, for example: methylthio, ethylthio, propylthio, butylthio, 2-cyanoethylthio, benzylthio, phenethylthio, 2-(diethylamino)ethylthio, ethoxyethylthio or phenoxyethylthio); a heteroarylthio radical (such as, for example: 5-phenyl-2,3,4,5-tetrazolylthio or 2-benzothiazolylthio); a heteroaryloxy radical (such as, for example: 5-phenyl-2,3,4,5-tetrazolyloxy or 2-benzothiazolyloxy); a thiocyano radical; an alkyloxythiocarbonylthio radical (such as dodecyloxythiocarbonylthio); a sulphonamido radical (such as benzenesulphonamido or N-ethyltoluenesulphonamido); a pentafluorobutanamido radical; a 2,3,4,5,6-pentafluorobenzamido radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; a 5,5-dimethyl-2,4-dioxo-3-oxazolidinyl radical; a 2-oxo-1,2-dihydro-1-pyridinyl radical; an alkylamido radical; an arylamido radical; an $NR^{III}R^{IV}$ radical with $R^{III}$ and $R^{IV}$, which are identical or different, representing a $C_1$–$C_4$ alkyl or a $C_1$–$C_4$ hydroxyalkyl; a carboxyl radical; an alkoxycarbonyl radical; an alkyloxycarbonylamino radical; an aryloxycarbonylamino radical; a sulphonyloxy radical, such as methanesulphonyloxy; an alkoxycarbonyloxy radical, such as methoxycarbonyloxy or ethoxycarbonyloxy; or an aryloxycarbonyloxy radical, such as phenyloxycarbonyloxy;

$Z_a$ and $Z_b$, which are different from one another, represent an oxygen or nitrogen atom;

$R_2$ and $R_3$, which are identical or different, represent a hydrogen atom; a linear or branched $C_1$–$C_{20}$ alkyl radical optionally substituted by 1 or 2 R radicals chosen from the group consisting of halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl; an aryl radical (such as phenyl or naphthyl) optionally substituted by 1 or 2 R radicals as defined above; or a 5- or 6-membered heterocycle having at least one nitrogen, oxygen or sulphur atom (such as pyridyl, quinolyl, pyrrolyl, morpholinyl, furanyl, tetrahydrofuranyl, pyrazolyl, triazolyl, tetrazolyl, thiazolyl, oxazolyl, imidazolyl or thiadiazolyl), optionally substituted by 1 or 2 R radicals as defined above;

when $R_2$ and/or $R_3$ denotes an alkyl radical, an aryl radical or a 5- or 6-membered heterocycle (as defined above), it can be connected to the carbon atom of the nucleus via an oxygen, nitrogen or sulphur atom (in this case, $R_2$ and/or $R_3$ become $XR_2$ and/or $XR_3$, with X=O, NH or S);

$R_2$ and $R_3$ can also denote a halogen atom (such as bromine, chlorine or fluorine); an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamido radical; an imido radical; a ureido radical; a sulphamoylamino radical; an alkoxycarbonylamino radical; an aryloxycarbonylamino radical; an alkoxycarbonyl radical; an aryloxycarbonyl radical; or a carboxyl radical;

and at least one oxidation base.

The addition salts with an acid of the compounds of the invention can be chosen in particular from hydrochlorides, hydrobromides, tartrates, tosylates, benzenesulphonates, sulphates, lactates and acetates.

Preference is given, among the $R_1$ radicals of the formula (I) defined above, to the radicals chosen from the group consisting of a hydrogen atom; a $C_1-C_4$ alkoxy radical; a phenoxy radical; a phenoxy radical substituted by a halogen atom, a $C_1-C_4$ alkyl, a carboxyl or a trifluoromethyl group; an acyloxy radical; a benzyloxy radical; a $C_1-C_4$ alkylthio radical; a phenylthio radical; a phenylthio radical substituted by a halogen atom, a $C_1-C_4$ alkyl, a carboxyl or a trifluoromethyl group; a $C_1-C_4$ alkylamido radical; a phenylamido radical; an $NR^{III}R^{IV}$ radical with $R^{III}$ and $R^{IV}$, which are identical or different, representing a $C_1-C_4$ alkyl or a $C_1-C_4$ hydroxyalkyl; a carboxyl; a $C_3-C_4$ alkoxycarbonyl radical; or a halogen atom, such as chlorine or bromine.

More particularly still, preference is given to the $R_1$ radicals chosen from the group consisting of hydrogen, chlorine, ethoxy, phenoxy, benzyloxy, acyloxy, acetamido and dimethylamino.

Preference is given, among the $R_2$ and $R_3$ radicals of the formula (I) defined above, to the radicals chosen from the group consisting of a hydrogen atom; a linear or branched $C_1-C_4$ alkyl; a phenyl; a phenyl substituted by a halogen atom, a $C_1-C_4$ alkyl, a $C_1-C_4$ alkoxy, a nitro group, an amino group, a trifluoromethyl group or a $C_1-C_4$ alkylamino group; a benzyl radical; a benzyl radical substituted by a halogen atom, a $C_1-C_4$ alkyl, a $C_1-C_4$ alkoxy, a nitro group, an amino group or a trifluoromethyl group; a $C_1-C_4$ alkylamino; a heterocycle chosen from thiophene, furan or pyridine; a trifluoromethyl radical; a $(CH_2)_p$—X—$(CH_2)_q$—OR' radical, where p and q are identical or different integers between 1 and 3, R' represents H or methyl and X denotes an oxygen atom or an NR" group with R" denoting hydrogen or methyl; a $C_1-C_4$ hydroxyalkyl; a $C_1-C_4$ aminoalkyl; a $C_1-C_4$ alkylamino; a $C_1-C_4$ dialkylamino; an arylamino; an alkoxy radical chosen from methoxy, ethoxy or phenoxy; a halogen chosen from chlorine, bromine or fluorine; a carboxyl group; a $C_1-C_4$ alkoxycarbonyl; a phenyloxycarbonyl; methylthio; ethylthio; phenylthio; methanesulphonyl or cyano.

More particularly still, preference is given to the $R_2$ and $R_3$ radicals of the formula (I) chosen from the group consisting of hydrogen; an alkyl chosen from methyl, ethyl, isopropyl or tert-butyl; a halogen chosen from fluorine and chlorine; phenyl; toluyl; 4-chlorophenyl; 4-methoxyphenyl; 3-methoxyphenyl; 2-methoxyphenyl; benzyl; a heterocycle chosen from pyridyl, furyl or thienyl; trifluoromethyl; hydroxymethyl; aminomethyl; methoxy or ethoxy; methylamino or ethylamino or dimethylamino; carboxyl; methoxycarbonyl or ethoxycarbonyl; or cyano.

More particularly still, preference is given to the $R_2$ and $R_3$ radicals chosen from the group consisting of a hydrogen atom; a methyl radical; ethyl; phenyl; toluyl; 4-chlorophenyl; 4-methoxyphenyl; benzyl; trifluoromethyl; chloro; a methoxy or ethoxy radical; a carboxyl radical; methylamino or dimethylamino; or cyano.

Mention may be made, among the preferred compounds of formula (I) of the invention, of those chosen from the group consisting of the compounds of formula (I) in which $R_1$ represents a hydrogen or chlorine atom and in which $R_2$ and $R_3$, which are identical or different, represent a hydrogen atom or a methyl, ethyl, isopropyl, phenyl, ethoxy, trifluoromethyl or methylthio radical.

Mention may be made, among the more particularly preferred compounds of formula (I) of the invention, of those chosen from the group consisting of:

2-methyl-6-phenylpyrrolo[3,2-d]oxazole
2,6-dimethylpyrrolo[3,2-d]oxazole
7-chloro-2-methyl-6-phenylpyrrolo[3,2-d]oxazole
8-methyl-4-phenylpyrrolo[3,2-d]oxazole
2-methyl-6-phenylpyrrolo[3,2-d]oxazole
4,8-dimethyl-6-phenylpyrrolo[3,2-d]oxazole.

The compounds of formula (I) of the present invention, their synthetic intermediates and their processes of preparation are disclosed in Japanese Patent Application JP 07 325 375, in the article J. Chem. Soc., 1948, 70, 2205, in Synthesis, 1970, 648, and in Patent Applications FR 2,074, 731 and EP 0,879,953.

The compound or compounds of formula (I) in accordance with the invention preferably represent from 0.0005 to 12% by weight approximately of the total weight of the dyeing composition and more preferably still from 0.005 to 6% by weight approximately of this weight.

The nature of the oxidation base or bases which can be used in the dyeing composition according to the invention is not critical. This or these oxidation bases are preferably chosen from para-phenylenediamines, bisphenylalkylenediamines, para-aminophenols, ortho-aminophenols, heterocyclic bases, and their addition salts with an acid.

Mention may in particular be made, among the para-phenylenediamines which can be used as oxidation bases in the dyeing composition according to the invention, of the compounds corresponding to the following formula (II) and their addition salts with an acid:

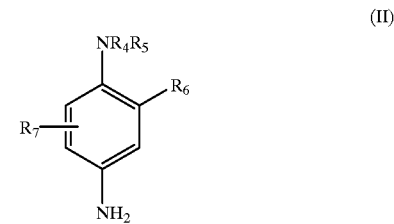

(II)

in which:

$R_4$ represents a hydrogen atom or a $C_1-C_4$ alkyl, $C_1-C_4$ monohydroxyalkyl, $C_2-C_4$ polyhydroxyalkyl or $(C_1-C_4)$alkoxy$(C_1-C_4)$alkyl radical, $R_5$ represents a hydrogen atom or a $C_1-C_4$ alkyl, $C_1-C_4$ monohydroxyalkyl or $C_2-C_4$ polyhydroxyalkyl radical, $R_6$ represents a hydrogen atom, a halogen atom, such as a chlorine atom, or a $C_1-C_4$ alkyl, sulpho, carboxyl, $C_1-C_4$ monohydroxyalkyl or $C_1-C_4$ hydroxyalkoxy radical, $R_7$ represents a hydrogen atom or a $C_1-C_4$ alkyl radical.

In the above formula (II) and when $R_6$ is other than a hydrogen atom, then $R_4$ and $R_5$ preferably represent a hydrogen atom and $R_6$ is preferably identical to $R_7$ and, when $R_6$ represents a halogen atom, then $R_4$, $R_5$ and $R_7$ preferably represent a hydrogen atom.

Mention may more particularly be made, among the para-phenylenediamines of above formula (II), of para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-[(β-methoxyethyl)amino]-benzene, 2-chloro-para-phenylenediamine, and their addition salts with an acid.

Mention may in particular be made, among the bisphenylalkylenediamines which can be used as oxidation bases in the dyeing composition according to the invention, of the compounds corresponding to the following formula (III) and their addition salts with an acid:

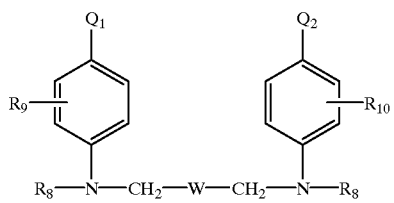

(III)

in which:

$Q_1$ and $Q_2$, which are identical or different, represent a hydroxyl or $NHR_{11}$ radical in which $R_{11}$ represents a hydrogen atom or a $C_1$–$C_4$ alkyl radical, $R_8$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amino residue can be substituted, $R_9$ and $R_{10}$, which are identical or different, represent a hydrogen or halogen atom or a $C_1$–$C_4$ alkyl radical, W represents a radical taken from the group consisting of the following radicals:

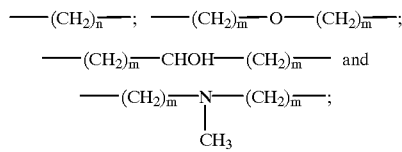

in which n is an integer of between 0 and 8 inclusive and m is an integer of between 0 and 4 inclusive.

Mention may more particularly be made, among the bisphenylalkylenediamines of above formula (III), of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-amino-phenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis (ethyl)-N,N'-bis(4'-amino-3'-methylphenyl)-ethylenediamine, and their addition salts with an acid.

Among these bisphenylalkylenediamines of formula (III), N,N'-bis(β-hydroxyethyl)-N,N'-bis(4'-aminophenyl)-1,3-diamino-2-propanol or one of its addition salts with an acid are particularly preferred.

Mention may in particular be made, among the para-aminophenols which can be used as oxidation bases in the dyeing composition according to the invention, of the compounds corresponding to the following formula (IV) and their addition salts with an acid:

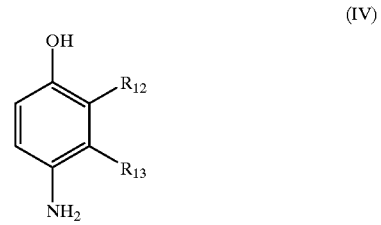

(IV)

in which:

$R_{12}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical, $R_{13}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy$(C_1$–$C_4)$alkyl radical, it being understood that at least one of the $R_{12}$ or $R_{13}$ radicals represents a hydrogen atom.

Mention may more particularly be made, among the para-aminophenols of above formula (IV), of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl) aminomethyl]phenol, and their addition salts with an acid.

Mention may in particular be made, among the ortho-aminophenols which can be used as oxidation bases in the dyeing composition according to the invention, of 2-aminophenol, 2-amino-1-hydroxy-5-methylbenzene, 2-amino-1-hydroxy-6-methylbenzene, 5-acetamido-2-aminophenol, and their addition salts with an acid.

Mention may in particular be made, among the heterocyclic bases which can be used as oxidation bases in the dyeing composition according to the invention, of pyridine derivatives, pyrimidine derivatives, pyrazole derivatives, and their addition salts with an acid.

Mention may more particularly be made, among the pyridine derivatives, of the compounds disclosed, for example, in Patents GB 1,026,978 and GB 1,153,196, such as 2,5-diaminopyridine, and their addition salts with an acid.

Mention may more particularly be made, among the pyrimidine derivatives, of the compounds disclosed, for example, in German Patent DE 2,359,399 or Japanese Patents JP 88-169,571 and JP 91-333,495, such as 2,4,5,6-tetraaminopyrimidine, 4-hydroxy-2,5,6-triaminopyrimidine, and their addition salts with an acid.

Mention may more particularly be made, among the pyrazole derivatives, of the compounds disclosed in Patents DE 3,843,892 and DE 4,133,957 and Patent Applications WO 94/08969 and WO 94/08970, such as 4,5-diamino-1-methylpyrazole, 3,4-diaminopyrazole and 4,5-diamino-1-(4'-chlorobenzyl)pyrazole, and their addition salts with an acid.

According to the invention, the oxidation base or bases preferably represent from 0.0005 to 12% by weight approximately of the total weight of the dyeing composition and more preferably still from 0.005 to 6% by weight approximately of this weight.

The dyeing composition according to the invention can also include one or more additional couplers other than the compounds of formula (I) and/or one or more direct dyes, so as to vary or enrich with highlights the shades obtained with the oxidation bases.

The additional couplers which can be used in the composition according to the invention can be chosen from couplers conventionally used in oxidation dyeing and among which may in particular be mentioned meta-phenylenediamines, meta-aminophenols, meta-diphenols and heterocyclic couplers, such as, for example, indole derivatives or indoline derivatives, and their addition salts with an acid.

These couplers can in particular be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl)amino-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, and their addition salts with an acid.

When they are present, these additional couplers preferably represent from 0.0005 to 5% by weight approximately of the total weight of the dyeing composition and more preferably still from 0.005 to 3% by weight approximately of this weight.

The addition salts with an acid of the oxidation base or bases and/or of the additional couplers which can be used in the dyeing composition of the invention are chosen in particular from hydrochlorides, hydrobromides, sulphates and tartrates, lactates and acetates.

The medium appropriate for dyeing (or vehicle) is generally composed of water or of a mixture of water and of at least one organic solvent, in order to dissolve the compounds which would not be sufficiently soluble in water. Mention may be Lade, for example, as organic solvent, of lower $C_1$–$C_4$ alcohols, such as ethanol and isopropanol, glycerol, glycols and glycol ethers, such as 2-butoxyethanol, propylene glycol, propylene glycol monomethyl ether, diethylene glycol monoethyl ether and diethylene glycol monomethyl ether, and aromatic alcohols, such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 12. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, carboxylic acids, such as tartaric acid, citric acid or lactic acid, or sulphonic acids.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of following formula (V):

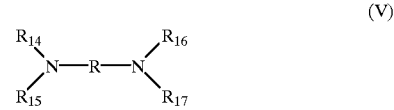

in which R is a propylene residue optionally substituted by a hydroxyl group or a $C_1$–$C_4$ alkyl radical; and $R_{14}$, $R_{15}$, $R_{16}$ and $R_{17}$, which are identical or different, represent a hydrogen atom or a $C_1$–$C_4$ alkyl or $C_1$–$C_4$ hydroxyalkyl radical.

The dyeing composition according to the invention can also include various adjuvants conventionally used in hair dyeing compositions, such as anionic, cationic, non-ionic, amphoteric or zwitterionic surface-active agents or their mixtures, anionic, cationic, non-ionic, amphoteric or zwitterionic polymers or their mixtures, inorganic or organic thickening agents, antioxidizing agents, penetration agents, sequestering agents, fragrances, buffers, dispersing agents, conditioning agents, such as, for example, silicones, film-forming agents, preserving agents or opacifying agents.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibres and in particular of human hair.

Another subject-matter of the invention is the use of the compounds of above formula (I) as coupler, in combination with at least one oxidation base, for the oxidation dyeing of keratinous fibres and in particular of human keratinous fibres, such as hair.

Another subject-matter of the invention is a process for the oxidation dyeing of keratinous fibres and in particular of human keratinous fibres, such as hair, employing the dyeing composition as defined above.

According to this process, at least one dyeing composition as defined above is applied to the fibres, the colour being developed at acidic, neutral or alkaline pH using an oxidizing agent which is added only at the time of use to the dyeing composition or which is present in an oxidizing composition applied simultaneously or sequentially in a separate fashion.

According to a particularly preferred embodiment of the dyeing process according to the invention, the dyeing composition described above is mixed, at the time of use, with an oxidizing composition comprising, in a medium appropriate for dyeing, at least one oxidizing agent present in an amount sufficient to develop a colouring. The mixture obtained is subsequently applied to the keratinous fibres and is left to stand for 3 to 50 minutes approximately, preferably 5 to 30 minutes approximately, after which the hair is rinsed, washed with a shampoo, rinsed again and dried.

The oxidizing agent present in the oxidizing composition as defined above can be chosen from oxidizing agents conventionally used for the oxidation dyeing of keratinous fibres and among which may be mentioned hydrogen peroxide, urea hydrogen peroxide, alkali metal bromates, or persalts, such as perborates and persulphates. Hydrogen peroxide is particularly preferred.

The pH of the oxidizing composition including the oxidizing agent as defined above is such that, after mixing with the dyeing composition, the pH of the resulting composition applied to the keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels, or in any other form appropriate for carrying out dyeing of keratinous fibres and in particular of human hair.

Another subject-matter of the invention is a dyeing multi-compartment device or kit or any other packaging system with several compartments, a first compartment of which includes the dyeing composition as defined above and a second compartment of which includes the oxidizing composition as defined above.

These devices can be equipped with a means allowing the desired mixture to be deposited on the hair, such as the devices disclosed in Patent FR-2,586,913 on behalf of the Applicant Company.

EXAMPLES

EXAMPLES 1 AND 2 OF A DYEING PROCESS IN ALKALINE MEDIUM

The following dyeing composition in accordance with the invention was prepared (contents in grams):

| | |
|---|---|
| 8-Methyl-4-phenylpyrrolo[3,2-d]oxazole (coupler) (*) | 0.594 g |
| 4-(2-Methoxyethylamino)aniline (oxidation base) | 0.498 g |
| Ethanol | 20.0 g |
| Aqueous ammonia comprising 20% of $NH_3$ | 10.0 g |
| Sodium metabisulphite | 0.228 g |
| Sequestering agent | q.s. |
| Demineralized water | q.s. for 100 g |

(*) 8-Methyl-4-phenylpyrrolo[3,2-d]oxazole is obtained according to one of the preparation processes disclosed in Japanese Patent Application JP 07 325 375, in the article J. Chem. Soc., 1948, 70, 2205, in Synthesis, 1970, 648, and in Patent Applications FR 2,074,731 and EP 0,879,953.

Example 1

At the time of use, the dyeing composition was mixed with an equal amount by weight of a $6 \times 10^{-3}$ mol % aqueous ammonium persulphate solution.

The mixture obtained was applied for 30 minutes to locks of permed or unpermed natural grey hair comprising 90% of white hairs in the proportion of 10 g per 1 g of hair. After rinsing, washing with a standard shampoo and drying the locks, powerful colourings are obtained which are not very selective in the range of the reds.

Example 2

At the time of use, the dyeing composition was mixed with an equal amount by weight of a 20-volume aqueous hydrogen peroxide solution.

The mixture obtained was applied for 30 minutes to locks of permed or unpermed natural grey hair comprising 90% of white hairs in the proportion of 10 g per 1 g of hair. After rinsing, washing with a standard shampoo and drying the locks, powerful colourings are obtained which are not very selective in the range of the reds.

EXAMPLES 3 AND 4 OF A DYEING PROCESS IN NEUTRAL MEDIUM

The following dyeing composition in accordance with the invention was prepared (contents in grams):

| | |
|---|---|
| 8-Methyl-4-phenylpyrrolo[3,2-d]oxazole (coupler) | 0.594 g |
| 4-(2-Methoxyethylamino)aniline (oxidation base) | 0.498 g |
| Ethanol | 20.0 g |
| $K_2HPO_4/KH_2PO_4$ (1.5 M/1 M) buffer | 10.0 g |
| Sodium metabisulphite | 0.228 g |
| Sequestering agent | q.s. |
| Demineralized water | q.s. for 100 g |

Example 3

At the time of use, the dyeing composition was mixed with an equal amount by weight of a $6 \times 10^{-3}$ mol % aqueous ammonium persulphate solution.

The mixture obtained was applied for 30 minutes to locks of permed or unpermed natural grey hair comprising 90% of white hairs in the proportion of 10 g per 1 g of hair. After rinsing, washing with a standard shampoo and drying the locks, powerful colourings are obtained which are not very selective in the range of the reds.

Example 4

At the time of use, the dyeing composition was mixed with an equal amount by weight of a 20-volume aqueous hydrogen peroxide solution.

The mixture obtained was applied for 30 minutes to locks of permed or unpermed natural grey hair comprising 90% of white hairs in the proportion of 10 g per 1 g of hair. After rinsing, washing with a standard shampoo and drying the locks, powerful colourings are obtained which are not very selective in the range of the reds.

What is claimed is:

1. A composition for oxidation dyeing of keratinous fibres comprising, in a medium appropriate for dyeing:

at least one coupler selected from pyrrolooxazole compounds of following formula (I) and acid addition salts thereof:

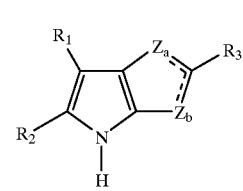

(I)

in which:

$R_1$ denotes: a hydrogen atom; a halogen atom; an alkoxy group; an aryloxy group; an acyloxy group; an arylthio group; an alkylthio group; a heteroarylthio group; a heteroaryloxy group; a thiocyano group; an alkyloxythiocarbonylthio group; a sulphonamido group; a pentafluorobutanamido group; a 2,3,4,5,6-pentafluorobenzamido group; a pyrazolyl group; an imidazolyl group; a triazolyl group; a tetrazolyl group; a benzimidazolyl group; a 1-benzyl-5-ethoxy-3-hydantoinyl group; a 1-benzyl-3-hydantoinyl group; a 5,5-dimethyl-2,4-dioxo-3- oxazolidinyl group; a 2-oxo-1,2-dihydro-1-pyridinyl group; an alkylamido group; an arylamido group; an $NR^{III}R^{IV}$ group, wherein $R^{III}$ and $R^{IV}$ are identical or different and denote a $C_1$–$C_4$ alkyl or a $C_1$–$C_4$ hydroxyalkyl group; a carboxyl group; an alkoxycarbonyl group; an alkyloxycarbonylamino group; an aryloxycarbonylamino group; a sulphonyloxy group; an alkoxycarbonyloxy group; or an aryloxycarbonyloxy group;

$Z_a$ and $Z_b$ are different from one another and denote an oxygen or nitrogen atom;

$R_2$ and $R_3$ are identical or different and denote a hydrogen atom; a linear or branched $C_1$–$C_{20}$ alkyl group unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl group; an aryl group unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl group; a 5- or 6-membered heterocycle group having at least one nitrogen, oxygen or sulphur atom, unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, or acyl group; a halogen atom; an acyl group; a sulphonyl group; a sulphinyl group; a phosphonyl group; a carbamoyl group; a sulphamoyl group; a cyano group; a carbamoyloxy group; a sulphonamido group; an imido group; a ureido group; a sulphamoylamino group; an alkoxycarbonylamino group; an aryloxycarbonylamino group; an alkoxycarbonyl group; an aryloxycarbonyl group; or a carboxyl group; and when $R_2$ and/or $R_3$ denotes said alkyl group, said aryl group or said 5- or 6-membered heterocycle group defined above, said $R_2$ and $R_3$ can be connected to the carbon atom of said at least one coupler via an oxygen, nitrogen or sulphur atom;

and at least one oxidation base, wherein said at least one coupler and said at least one oxidation base are present in amounts effective to dye said keratinous fibers.

2. A composition according to claim 1, wherein said keratinous fibres are human keratinous fibres.

3. A composition according to claim 2, wherein said human keratinous fibres are hair.

4. A composition according to claim 1, wherein said $R_1$ of formula (I) is methoxy, ethoxy, propyloxy, benzyloxy, methoxyethoxy, phenoxyethoxy, 2-cyanoethoxy, phenethyloxy, p-chlorobenzyloxy, methoxyethylcarbamoyl-methoxy, phenoxy, 4-methoxyphenoxy, 4-nitrophenoxy, 4-cyanophenoxy, 4-methanesulphon-amidophenoxy, 4-methanesulphonylphenoxy, 3-methylphenoxy, 1-naphthyloxy, acetoxy, propanoyloxy, benzoyloxy, 2,4-dichlorobenzoyloxy, ethoxyoxaloyloxy, pyruvoyloxy, cinnamoyloxy, myristoyloxy, phenylthio, 4-carboxyphenylthio, 2-ethoxy-5-tert-butylphenylthio, 2-carboxyphenyl-thio, 4-methanesulphonylphenylthio, methylthio, ethylthio, propylthio, butylthio, 2-cyanoethylthio, benzylthio, phenethylthio, 2-(diethylamino)ethylthio, ethoxyethylthio, phenoxyethylthio, 5-phenyl-2,3,4,5-tetrazolylthio, 2-benzothiazolylthio, 5-phenyl-2,3,4,5-tetrazolyloxy, 2-benzothiazolyloxy, dodecyloxythiocarbonylthio, benzenesulphonamido, or N-ethyltoluenesulphonamido group; and/or wherein said $R_2$ and $R_3$ of the formula (I) are identical or different and denote phenyl, naphthyl, pyridyl, quinolyl, pyrrolyl, morpholinyl, furanyl, tetrahydrofuranyl, pyrazolyl, triazolyl, tetrazolyl, thiazolyl, oxazolyl, imidazolyl, or thiadiazolyl group, bromine, chlorine, or fluorine atom.

5. A composition according to claim 1, wherein said $R_1$ of the formula (I) is a hydrogen atom; a $C_1$–$C_4$ alkoxy group; a phenoxy group; a phenoxy group substituted by a halogen atom, a $C_1$–$C_4$ alkyl, a carboxyl or a trifluoromethyl group; an acyloxy group; a benzyloxy group; a $C_1$–$C_4$ alkylthio group; a phenylthio group; a phenylthio group substituted by a halogen atom, a $C_1$–$C_4$ alkyl, a carboxyl or a trifluoromethyl group; a $C_1$–$C_4$ alkylamido group; a phenylamido group; an $NR^{III}R^{IV}$ group, wherein $R^{III}$ and $R^{IV}$ are identical or different and denote a $C_1$–$C_4$ alkyl group or a $C_1$–$C_4$ hydroxyalkyl group; a carboxyl group; a $C_1$–$C_4$ alkoxycarbonyl group; or a halogen atom.

6. A composition according to claim 1, wherein said $R_1$ of the formula (I) is a hydrogen atom, a chlorine atom, ethoxy, phenoxy, benzyloxy, acyloxy, acetamido or dimethylamino group.

7. A composition according to claim 1, wherein said $R_2$ and $R_3$ of the formula (I) are identical or different and denote a hydrogen atom; a linear or branched $C_1$–$C_4$ alkyl group; a phenyl group; a phenyl group substituted by a halogen atom, a $C_1$–$C_4$ alkyl group, a $C_1$–$C_4$ alkoxy group, a nitro group, an amino group, a trifluoromethyl group or a $C_1$–$C_4$ alkylamino group; a benzyl group; a benzyl group substituted by a halogen atom, a $C_1$–$C_4$ alkyl group, a $C_1$–$C_4$ alkoxy group, a nitro group, an amino group or a trifluoromethyl group; a $C_1$–$C_4$ alkylamino group; a heterocycle group, wherein said heterocycle group is thiophene, furan or pyridine group; a trifluoromethyl group; a $(CH_2)_p$—X—$(CH_2)_q$—OR' group, wherein p and q are identical or different integers ranging from 1 to 3, R' denotes an H atom or methyl group and X denotes an oxygen atom or an NR" group wherein R" denotes a hydrogen atom or methyl group; a $C_1$–$C_4$ hydroxyalkyl group; a $C_1$–$C_4$ aminoalkyl group; a $C_1$–$C_4$ alkylamino group; a $C_1$–$C_4$ dialkylamino group; an arylamino group; an alkoxy group, wherein said alkoxy group is methoxy, ethoxy or phenoxy; a halogen atom, wherein said halogen atom is chlorine, bromine or fluorine atom; a carboxyl group; a $C_1$–$C_4$ alkoxycarbonyl group; a phenyloxycarbonyl group; methylthio group; ethylthio group; phenylthio group; methanesulphonyl group; or cyano group.

8. A composition according to claim 7, wherein said $R_2$ and $R_3$ of the formula (I) are identical or different and denote a hydrogen atom; an alkyl group, wherein said alkyl group is methyl, ethyl, isopropyl or tert-butyl; a halogen atom, wherein said halogen atom is fluorine or chlorine; phenyl group; toluyl group; 4-chlorophenyl group; 4-methoxyphenyl group; 3-methoxyphenyl group; 2-methoxyphenyl group; benzyl group; a heterocycle group, wherein said heterocycle group is pyridyl, furyl or thienyl; trifluoromethyl group; hydroxymethyl group; aminomethyl group; methoxy or ethoxy group; methylamino or ethylamino or dimethylamino group; carboxyl group; methoxycarbonyl or ethoxycarbonyl group; or cyano group.

9. A composition according to claim 8, wherein said $R_2$ and $R_3$ of the formula (I) are identical or different and denote a hydrogen atom; a methyl group; an ethyl group; phenyl group; toluyl group; 4-chlorophenyl group; 4-methoxyphenyl group; benzyl group; trifluoromethyl group; a chlorine atom; a methoxy or ethoxy group; a carboxyl group; methylamino or dimethylamino group; or cyano group.

10. A composition according to claim 1, wherein in said at least one coupler, $R_1$ denotes a hydrogen or chlorine atom; $R_2$ and $R_3$ are identical or different and denote a hydrogen atom or a methyl, ethyl, isopropyl, phenyl, ethoxy, trifluoromethyl or methylthio group.

11. A composition according to claim 1, wherein said acid addition salts are selected from hydrochlorides, hydrobromides, sulphates, tartrates, benzenesulphonates, lactates, tosylates, and acetates.

12. A composition according to claim 1, wherein the amount of said at least one coupler ranges from about 0.0005 to about 12% by weight of the total weight of the dyeing composition.

13. A composition according to claim 12, wherein the amount of said at least one coupler ranges from about 0.005 to about 6% by weight of the total weight of the dyeing composition.

14. A composition according to claim 1, wherein said at least one oxidation base is a para-phenylenediamine, a bisphenylalkylenediamine, a para-aminophenol, an ortho-aminophenol, a heterocyclic base, or an acid addition salt thereof.

15. A composition according to claim 1, wherein the amount of said at least one oxidation base ranges from about 0.0005 to about 12% by weight of the total weight of the dyeing composition.

16. A composition according to claim 15, wherein the amount of said at least one oxidation base ranges from about 0.005 to about 6% by weight of the total weight of the dyeing composition.

17. A composition according to claim 1, further comprising at least one additional coupler other than said at least one coupler of formula (I) and/or at least one direct dye.

18. A composition according to claim 1, wherein said medium appropriate for dyeing comprises water or a mixture of water and of at least one organic solvent, wherein said at least one organic solvent is a lower $C_1$–$C_4$ alcohol, glycerol, a glycol or a glycol ether, or an aromatic alcohol.

19. A composition according to claim 18, wherein said at least one organic solvent is ethanol, isopropanol, 2-butoxyethanol, propylene glycol, propylene glycol monomethyl ether, diethylene glycol monoethyl ether, diethylene glycol monomethyl ether, benzyl alcohol, or phenoxyethanol.

20. A composition according to claim 1, having a pH ranging from about 3 to about 12.

21. A composition according to claim 20, having a pH ranging from about 5 to about 11.

22. A composition according to claim 1, wherein said composition is in the form of a liquid, a cream, or a gel, or in any other form appropriate for carrying out dyeing of keratinous fibres.

23. A method for the production of an oxidation dyeing composition for the oxidation dyeing of keratinous fibres, which comprises incorporating into said composition, a medium appropriate for dyeing, at least one coupler chosen from pyrrolooxazole compounds of following formula (I) and acid addition salts thereof:

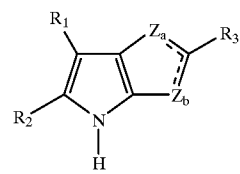

in which:

$R_1$ is chosen from: a hydrogen atom; a halogen atom; an alkoxy group; an aryloxy group; an acyloxy group; an arylthio group; an alkylthio group; a heteroarylthio group; a heteroaryloxy group; a thiocyano group; an alkyloxythiocarbonylthio group; a sulphonamido group; a pentafluorobutanamido group; a 2,3,4,5,6-pentafluorobenzamido group; a pyrazolyl group; an imidazolyl group; a triazolyl group; a tetrazolyl group; a benzimidazolyl group; a 1-benzyl-5-ethoxy-3-hydantoinyl group; a 1-benzyl-3-hydantoinyl group; a 5,5-dimethyl-2,4-dioxo-3-oxazolidinyl group; a 2-oxo-1,2-dihydro-1-pyridinyl group; an alkylamido group; an arylamido group; an $NR^{III}R^{IV}$ group, wherein $R^{III}$ and $R^{IV}$ are identical or different and denote a $C_1$–$C_4$ alkyl or a $C_1$–$C_4$ hydroxyalkyl group; a carboxyl group; an alkoxycarbonyl group; an alkyloxycarbonylamino group; an aryloxycarbonylamino group; a sulphonyloxy group; an alkoxycarbonyloxy group; or an aryloxycarbonyloxy group;

$Z_a$ and $Z_b$ are different from one another and are chosen from an oxygen or nitrogen atom;

$R_2$ and $R_3$ are identical or different and are chosen from a hydrogen atom; a linear or branched $C_1$–$C_{20}$ alkyl group unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl group; an aryl group unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl or acyl group; a 5- or 6-membered heterocycle group having at least one nitrogen, oxygen or sulphur atom, unsubstituted or substituted by one or two R groups, wherein said R group is independently selected from a halogen atom, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, or acyl group; a halogen atom; an acyl group; a sulphonyl group; a sulphinyl group; a phosphonyl group; a carbamoyl group; a sulphamoyl group; a cyano group; a siloxy group; an amino group, an acylamino group; an acyloxy group; a carbamoyloxy group a sulphonamido group; an imido group; a ureido group; a sulphamoylamino group; an alkoxycarbonylamino group; an aryloxycarbonylamino group; an alkoxycarbonyl group; an aryloxycarbonyl group; or a carboxyl group; and when $R_2$ and/or $R_3$ are chosen from said alkyl group, said aryl group or said 5- or 6-membered heterocycle group defined above, said $R_2$ and $R_3$ can be connected to the carbon atom of said at least one coupler via an oxygen, nitrogen or sulphur atom;

and at least one oxidation base, wherein said at least one coupler and said at least one oxidation base are present in amounts effective to dye said keratinous fibers.

24. A process for oxidation dyeing of keratinous fibres comprising applying to said keratinous fibres at least one dyeing composition according to claim 1, developing a color at an acidic, neutral or alkaline pH with an oxidizing agent, wherein said oxidizing agent is added to the dyeing composition only at the time of application, or wherein said oxidizing agent is present in an oxidizing composition and said oxidizing composition is applied simultaneously or sequentially with said at least one dyeing composition.

25. A process according to claim 24, wherein said at least one dyeing composition comprising said oxidizing agent is left standing on said keratinous fibres after said application and thereafter comprising the additional step of rinsing.

26. A process according to claim 25, wherein said at least one dyeing composition comprising said oxidizing agent is left standing on said keratinous fibres for an amount of time ranging from 3 to 50 minutes after said application and before said rinsing.

27. A process according to claim 26, wherein said at least one dyeing composition comprising said oxidizing agent is left standing on said keratinous fibres for an amount of time ranging from 5 to 30 minutes after said application and before said rinsing.

28. A process according to claim 24, wherein said oxidizing agent is hydrogen peroxide, urea hydrogen peroxide, an alkali metal bromate, or a persalt.

29. A process according to claim 28, wherein said persalt is a perborate or a persulphate.

30. A process according to claim 28, wherein said oxidizing agent is hydrogen peroxide.

31. A process according to claim 24, wherein said keratinous fibres are human hair.

32. A multi-compartment dyeing device or kit for dyeing keratinous fibres comprising at least two compartments, wherein, a first compartment comprises a dyeing composition according to claim 1 and a second compartment comprises an oxidizing composition.

33. A composition for oxidation dyeing of keratinous fibers comprising:

at least one coupler selected from
2-methyl-6-phenylpyrrolo[3,2-d]oxazole,
2,6-dimethylpyrrolo[3,2-d]oxazole,
7-chloro-2-methyl-6-phenylpyrrolo[3,2-d]oxazole,
8-methyl-4-phenylpyrrolo[3,2-d]oxazole,
2-methyl-6-phenylpyrrolo[3,2-d]oxazole, and
4,8-dimethyl-6-phenylpyrrolo[3,2-d]oxazole;

and at least one oxidation base, wherein said at least one coupler and said at least one oxidation base are present in amounts effective to dye said keratinous fibers.

* * * * *

UNITED STATES PATENT AND TRADEMARK OFFICE
CERTIFICATE OF CORRECTION

PATENT NO.   : 6,063,136
DATED        : July 3, 2000
INVENTOR(S)  : Laurent Vidal, Paris; Gérard Malle, Villiers-sur-Morin It is certified that error appears in the above-identified patent and that said Letters Patent is hereby corrected as shown below:

Column 11, claim 1,
Line 37, after "cyano group;" should read -- a siloxy group; an amino group; an acylamino group; an acyloxy group; --.

Signed and Sealed this

Twenty-ninth Day of January, 2002

Attest:

Attesting Officer

JAMES E. ROGAN
Director of the United States Patent and Trademark Office